United States Patent
Boussad

(10) Patent No.: US 10,866,228 B2
(45) Date of Patent: Dec. 15, 2020

(54) ASPHALT EMULSION FORMULATION TOOL

(71) Applicant: ExxonMobil Research and Engineering Company, Annandale, NJ (US)

(72) Inventor: Nadjib Boussad, Bois Guillaume (FR)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 468 days.

(21) Appl. No.: 15/988,031

(22) Filed: May 24, 2018

(65) Prior Publication Data

US 2018/0348189 A1 Dec. 6, 2018

Related U.S. Application Data

(60) Provisional application No. 62/512,801, filed on May 31, 2017.

(51) Int. Cl.
G01N 33/28 (2006.01)
G01N 33/44 (2006.01)
(Continued)

(52) U.S. Cl.
CPC ........ G01N 33/2823 (2013.01); C08L 95/005 (2013.01); G01N 11/00 (2013.01);
(Continued)

(58) Field of Classification Search
CPC .. G01N 33/2823; G01N 11/00; G01N 33/442; G01N 2011/0026; C08L 95/005; G05B 13/048
(Continued)

(56) References Cited

U.S. PATENT DOCUMENTS

| 4,832,747 A | 5/1989 | Marchal |
| 6,384,112 B1 | 5/2002 | Boussad |

(Continued)

FOREIGN PATENT DOCUMENTS

| WO | 1992/019683 A1 | 11/1992 |
| WO | 1996/04427 A1 | 2/1996 |
| WO | 9714953 A1 | 4/1997 |

OTHER PUBLICATIONS

The International Search Report and Written Opinion of PCT/US2018/034286 dated Oct. 12, 2018.

(Continued)

Primary Examiner — John H Le

(74) Attorney, Agent, or Firm — Robert A. Migliorini

(57) ABSTRACT

Methods are provided for predicting the properties of an asphalt emulsion, such as an asphalt emulsion that contains an asphalt fraction derived from a plurality of crude oils. Corresponding tools are provided to allow for visualization of the predicted asphalt emulsion properties. The properties of the asphalt components in an asphalt fraction for forming an emulsion can be represented based on using a simplified functional form to represent each emulsion property of each asphalt component. The emulsion properties of an asphalt fraction, composed of a plurality of asphalt components, can be modeled based on a linear combination of the emulsion properties of the asphalt components.

20 Claims, 10 Drawing Sheets

(51) Int. Cl.
  *G01N 11/00*   (2006.01)
  *G05B 13/04*   (2006.01)
  *C08L 95/00*   (2006.01)

(52) U.S. Cl.
  CPC ......... *G01N 33/442* (2013.01); *G05B 13/048* (2013.01); *G01N 2011/0026* (2013.01)

(58) Field of Classification Search
  USPC .......................................................... 702/30
  See application file for complete search history.

(56) References Cited

U.S. PATENT DOCUMENTS

| | | | |
|---|---|---|---|
| 8,968,551 B2* | 3/2015 | Moran | C10C 3/06 208/39 |
| 2005/0050009 A1 | 3/2005 | Gardner et al. | |
| 2013/0104772 A1* | 5/2013 | Schabron | B01F 17/0014 106/277 |
| 2014/0156241 A1 | 6/2014 | Kumar et al. | |
| 2018/0196778 A1 | 7/2018 | Glaser et al. | |

OTHER PUBLICATIONS

Ronald et al., "Asphalt emulsions formulation: State-of-the-art and dependency of formulation on emulsions properties", Construction and Building Materials, 123 (2016) 162-173.

Alade et al., "Development of models to predict the viscosity of a compressed Nigerian bitumen and rheological property of its emulsions", Journal of Petroleum Science and Engineering, 145 (2016) 711-722.

* cited by examiner

P1: Emulsion property 1
P2: Emulsion property 2
X: Crude proportion in slate

ASPHALT EMULSION FORMULATION TOOL

CROSS-REFERENCE TO RELATED APPLICATIONS

This application claims the benefit of U.S. Provisional Application No. 62/512,801, filed on May 31, 2017, the entire contents of which are incorporated herein by reference.

FIELD

Systems and methods are provided for predicting properties of asphalt emulsions.

BACKGROUND

Asphalt is one of the world's oldest engineering materials, having been used since the beginning of civilization. Asphalt is a strong, versatile and chemical-resistant binding material that adapts itself to a variety of uses. For example, asphalt is used to bind crushed stone and gravel into firm tough surfaces for roads, streets, and airport runways. Asphalt, also known as pitch, can be obtained from either natural deposits, or as a by-product of the petroleum industry. Natural asphalts were extensively used until the early 1900s. The discovery of refining asphalt from crude petroleum and the increasing popularity of the automobile served to greatly expand the asphalt industry. Modern petroleum asphalt has the same durable qualities as naturally occurring asphalt, with the added advantage of being refined to a uniform condition substantially free of organic and mineral impurities.

The raw material used in modern asphalt manufacturing is petroleum, which is naturally occurring liquid bitumen. Asphalt is a natural constituent of petroleum, and there are crude oils that are almost entirely asphalt. The crude petroleum is separated into its various fractions through a distillation process. After separation, these fractions are further refined into other products such as asphalt, paraffin, gasoline, naphtha, lubricating oil, kerosene and diesel oil. Since asphalt is the base or heavy constituent of crude petroleum, it does not evaporate or boil off during the distillation process. Asphalt is essentially the heavy residue of the oil refining process. Asphalt can be used pure as a component in various applications, such as paving and roofing. Optionally, asphalt can also be modified with additives or polymers to improve final product performance and/or provided as an emulsion to reduce the severity of the conditions required for use of the asphalt/formation of products from the asphalt, such as reducing the temperature during use or product formation.

Asphalt emulsions produced in specific plants (mills) are generally composed of bitumen, water, additives, and emulsifier agents. Asphalt emulsions allow the production and placement of asphalt pavement at lower temperatures (less than 100° C.) than traditional hot mix asphalt, helping to reduce fuel use and fume emissions.

Emulsion characteristics can depend upon a variety of parameters such as emulsifier type and concentration, pH, binder and soap temperature, shear, and/or salt content. Despite the significant effort put into emulsion formulation development, failures during application can still occur over time due to, for example, unanticipated changes in asphalt emulsion components (such as emulsifier batch quality) and/or asphalt supply source.

Because asphalt is a residue from an oil refining process, if a blend of oils from more than one crude source is used as an input, the resulting asphalt residue will also represent a combination of the oils. Due to lower reliability of resulting asphalt quality prediction for forming an emulsion, asphalt end users that produce asphalt emulsions typically limit asphalt purchases to asphalts from known crudes and/or known combinations of crudes. This can limit the ability of a refiner to change crude slates, as the resulting asphalt from a new crude slate may not be considered for use and/or purchase by asphalt end users.

SUMMARY

In various aspects, methods and tools are provided for prediction of asphalt emulsion properties and corresponding visualization of the predicted asphalt emulsion properties. The methods and tools are based in part on the unexpected discovery that emulsion properties for an asphalt fraction can be effectively represented based on a linear combination of emulsion properties for the asphalt components in the asphalt fraction. This linear behavior is in contrast to the expected non-linear behavior observed when attempting to model or predict properties for asphalt fractions. Based on the ability to perform effective prediction of asphalt emulsion properties, the methods and tools can further allow for visualization of the relationship in emulsion properties between new asphalt fractions and other comparative asphalt fractions.

DETAILED DESCRIPTION

Figure 1:
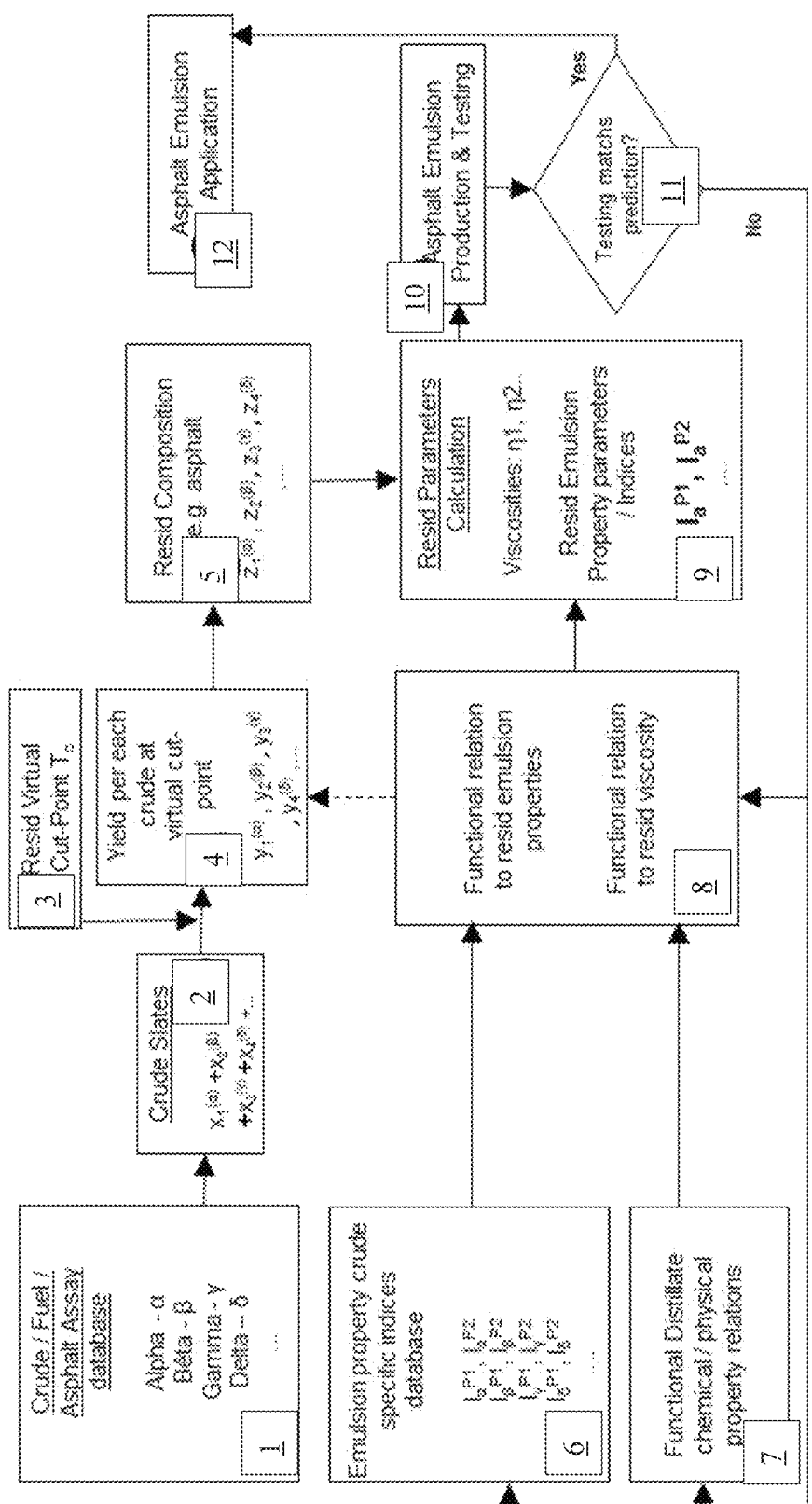
FIG. 1 shows a flowchart of creating a predictive model for properties and "emulsion indices" of asphalts produced from crude blends according to an embodiment of the invention.

All numerical values within the detailed description and the claims herein are modified by "about" or "approximately" the indicated value, and take into account experimental error and variations that would be expected by a person having ordinary skill in the art.

Overview

In various aspects, systems and methods are provided for predicting the properties of an asphalt emulsion, such as an asphalt emulsion that contains an asphalt fraction derived from a plurality of crude oils. It has been unexpectedly discovered that the properties of the asphalt components in an asphalt fraction for forming an emulsion can be represented based on using a simplified functional form to represent each emulsion property of each asphalt component. Using a simplified functional form (such as a polynomial with four terms or less) for each emulsion property provides sufficient degrees of freedom to allow for effective prediction of emulsion properties of individual asphalt components. It has further been discovered that the emulsion properties of an asphalt fraction, composed of a plurality of asphalt components, can be modeled based on a linear combination of the emulsion properties of the asphalt components. This ability to represent the emulsion properties of an asphalt fraction based on a linear combination of simplified functional forms associated with the asphalt components can allow for prediction of emulsion properties for a wide variety of asphalt fractions, so long as the emulsion properties of the underlying asphalt components have been sufficiently characterized. Fortunately, sufficient characterization of a given asphalt component can be achieved based on experimental measurements on asphalt fractions that include the given asphalt component. Thus, a model can be used to make predictions, for example, of emulsion viscosity and breaking index for an emulsion based on the asphalt fraction. In addition to the parameters for characterization of each emulsion property for each asphalt component, other parameters in the model can include (for example) the type of emulsifier, the water content of the emulsion, the temperature of the various components used to form the emulsion, and the viscosity of asphalt fraction.

In various aspects, the predicted properties of an emulsion based on an asphalt fraction can be incorporated into a tool for identifying changes in the emulsification conditions that would allow an emulsion to have, for example, an emulsion viscosity and breaking index within desired ranges. Based on a proposed set of conditions and an asphalt fraction for forming an emulsion, the tool can provide modifications to the proposed set of emulsification conditions to produce an emulsion matching desired limits of emulsion viscosity and breaking index. For example, a commercial solver can be used to perform a constrained optimization on the emulsion formation conditions to identify an emulsion having a combination of emulsion properties within a desired bounding area or other multi-dimensional bounding volume.

Additionally or alternately, an asphalt emulsion prediction tool as described herein can provide a further technical benefit in the form enhancing the ability of a user to visualize the relationships between a proposed asphalt emulsion formulation and prior asphalt emulsions. For example, producers of asphalt emulsions can typically have a set of asphalt fractions that have been previously used to form emulsions that are considered desirable or successful. When a new set of emulsion formation conditions is proposed, the asphalt emulsion prediction tool can be used to model the emulsion properties for emulsions based on these previously successful asphalt fractions under the new emulsion formulation conditions. A bounding shape, such as a bounding box, can then be created so that all of the predicted emulsions based on the previously successful asphalt fractions are captured within the bounding shape. The predicted emulsion properties for an emulsion based on a new asphalt fraction under the new emulsion conditions can then be compared with the bounding shape to determine whether the new asphalt fraction results in a predicted emulsion that falls within the bounding shape. This can allow a user to readily visualize whether an emulsion based on a new asphalt fraction is likely to fall within a range of properties similar to prior successful asphalt fractions, even though the new emulsion formation conditions are not the same as the conditions used for forming emulsions based on the prior asphalt fractions. The ability to provide this type of visualization tool is enabled, in part, by the unexpected discovery that emulsion properties for an asphalt fraction can be represented as a linear combination of the emulsion properties for the constituent asphalt components in the asphalt fraction.

For conventional emulsion production, formulations are typically developed for desired end-use pavement or roofing applications based on selected raw materials. In addition to selection of emulsifier(s) and fluxing agent(s), the raw materials can include an asphalt fraction derived from specific types of crudes. However, even asphalts derived from crude oils having the same designation can often have varying composition depending on when and/or where the crude oil was extracted. For example, processing changes within a refinery can result in changes in the cut point used for producing an asphalt fraction from a crude slate. As a result, the quality of emulsions produced by conventional methods can vary.

The difficulties in producing a desired emulsion can also limit the types of asphalts that are used for production of emulsions. In order to reduce or minimize the amount of required testing, conventional producers of emulsions can often limit the asphalts used for emulsion formation to asphalts produced from known crude slates. This can present difficulties for refiners of crude oils, since a change in the crude slate could result in an inability to find a suitable market for an asphalt fraction from a new crude slate.

In order to overcome one or more of the above difficulties, a predictive model can be used to allow for prediction of how an asphalt fraction derived from a crude slate (such as by distillation at a distillation cut point) will compare with prior asphalt fractions with respect to production of emulsions. The results from the predictive model can then be used in conjunction with a formulation tool to allow for modification of the conditions for a proposed emulsion formulation. This can allow for identification of conditions for forming an emulsion with a desired range of values for emulsion viscosity and breaking index.

It has been unexpectedly discovered that the emulsion properties of an asphalt fraction can be effectively represented using a linear model (such as a weighted average) based on emulsion properties of the asphalt components (i.e., components from different crude sources) in the asphalt fraction. Linear models have previously been used for modeling of blends of lighter crude fractions. Linear models are conventionally believed to be more suitable for lighter fractions in part due to the relatively low number of distinct species within a lighter fraction. Additionally, lighter fractions that correspond to a blend of lighter crude components tend to have minimal amounts of non-linear interactions between components within the fractions. By contrast, the properties of an asphalt fraction that corresponds to a blend of asphalt components have traditionally been difficult to predict based on a simple linear combination of the individual asphalt components. Asphalt compositions often include a large number of species that may not be well understood. Additionally, due to the complexity of asphalt fractions, the plurality of asphalt components within a blend can have significant interactions, so that the properties of an asphalt blend do not correspond well to a simple linear combination of properties based on the cut point used to separate the blended asphalt from an original blended feed. In spite of the prior difficulties in modeling asphalt fractions as a linear combination of asphalt components from different sources, it has been unexpectedly discovered that for prediction of asphalt emulsion properties, a model based on linear combinations of emulsion properties of the asphalt components within an asphalt fraction can be suitable.

In this discussion, reference will be made to crude sources, asphalt fractions, asphalt components, and feed components. An asphalt fraction represents an asphalt fraction made in any convenient manner, such as an asphalt fraction formed by distillation of a suitable feedstock at a suitable cut point temperature. An asphalt component is defined herein to refer to an asphalt fraction that is derived from a single crude source. Thus, a feedstock formed from a plurality of crude sources will result in formation of an asphalt fraction that contains a plurality of asphalt components. Similarly, a feed component is defined herein as a portion of a feed that is derived from a single crude source. A crude source is defined herein as a combination of a) a source of oil, tar sands, or another type of petroleum that can be used to form a crude oil stream, and b) any processing that is used to form such a crude oil stream prior to distilling the crude oil stream to form the asphalt fraction. Thus, use of a different distillation cut point during asphalt formation does not impact the source of a crude oil stream. However, two crude oil streams extracted from the same location, but that undergo different processing and/or separation procedures prior to reaching a refinery could be considered as crude oil streams from different sources.

Preferably, the emulsion properties for an asphalt fraction containing multiple asphalt components can be predicted based on representing each emulsion property of each asphalt component in an asphalt fraction using a simple polynomial form, such as a polynomial form comprising four terms or less. In order to fit the emulsion property parameters for various asphalt components, a plurality of asphalt fractions can be characterized in various types of emulsions to determine emulsion properties. The data from the emulsions based on asphalt fractions including multiple asphalt components can then be used to determine polynomial coefficients for individual components (such as by regression analysis). The properties of an asphalt component for forming an emulsion can then be represented, for example, using an "A+Bx" type functional form (i.e., a two-term polynomial) for each property, where "A" and "B" represent constants associated with an asphalt component from a particular crude source and "x" represents a mathematical function of the cut point temperature that was used to form the asphalt component. It is noted that the "cut point temperature" used for forming an asphalt component can correspond to a virtual cut point, as further described herein. The parameters "A" and "B" can be specific to each separate type of emulsion property to be predicted. The parameters "A" and "B" can be independent parameters or can be dependent parameters that have a defined relationship.

In order to use the model, a crude slate that is used to form an asphalt fraction can be specified, along with a cut point used to form the fraction. Based on the cut point, the proportion of each asphalt component in the asphalt fraction can be determined. The emulsion properties of the asphalt fraction can then be represented using a linear combination of the simple polynomial representations (such as "A+Bx") for each property of each asphalt component, with the weight of each component in the asphalt fraction corresponding to the weighting coefficient in the linear combination. Additionally, the penetration and viscosity values of the asphalt fraction can be determined or specified.

When using the model, in addition to specifying the properties of the asphalt fraction, an initial desired set of conditions for forming an emulsion can be specified. These conditions can include, but are not limited to, a water content for the emulsion; temperatures for one or more components of the emulsion; and/or the type and amount of emulsifier. The model can then provide predicted values, for example, for the emulsion viscosity and the breaking index based on the asphalt fraction and the other emulsion parameters. Optionally, the model can be used as part of a tool for providing improved emulsion formulation parameters adapted to a new asphalt composition. In such a tool, in addition to providing emulsion viscosity and breaking index values based on the input parameters, the tool can also provide suggested changes to the emulsion formulation parameters to allow the resulting emulsion to fall within a desired range or bounding shape of property values, such as a desired range of values for viscosity and breaking index.

Figure 3:
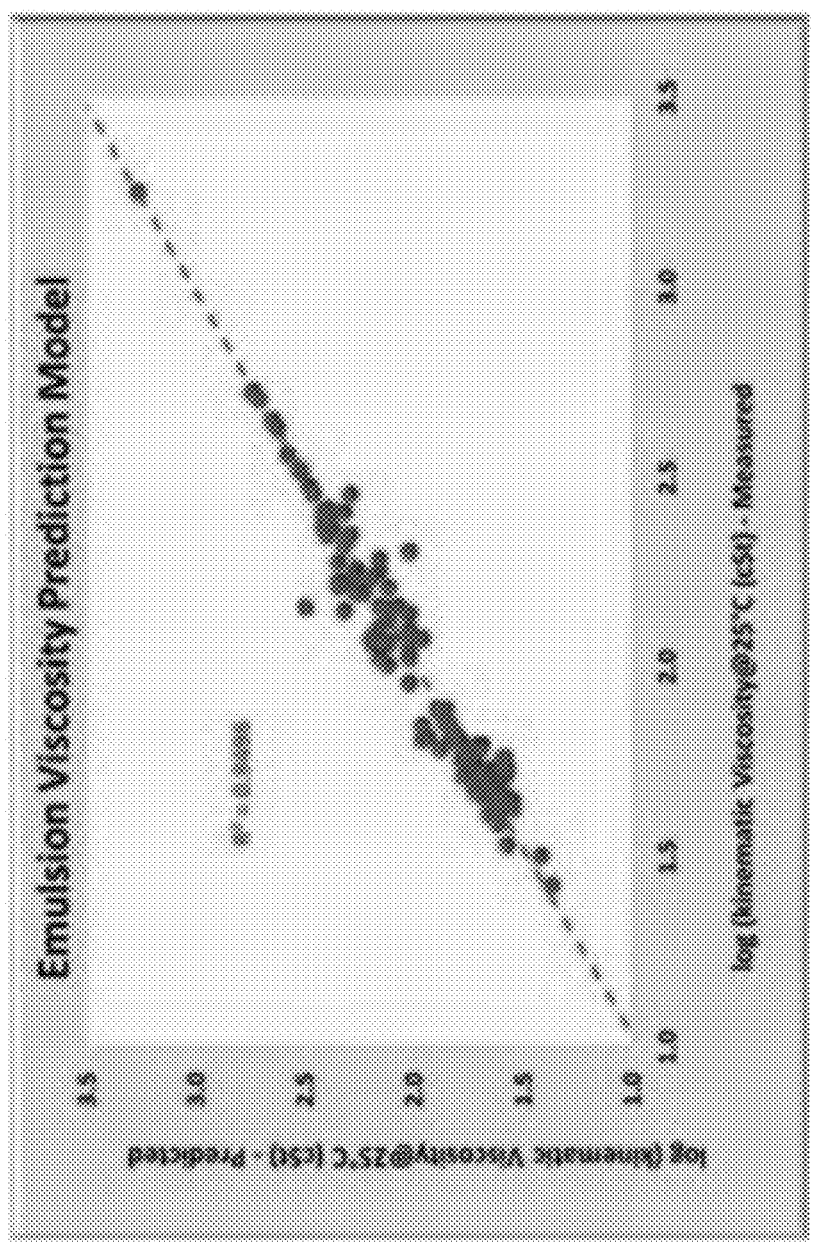
FIG. 3 shows a comparison of measured and calculated viscosity values for a variety of asphalt emulsions.
Figure 4:
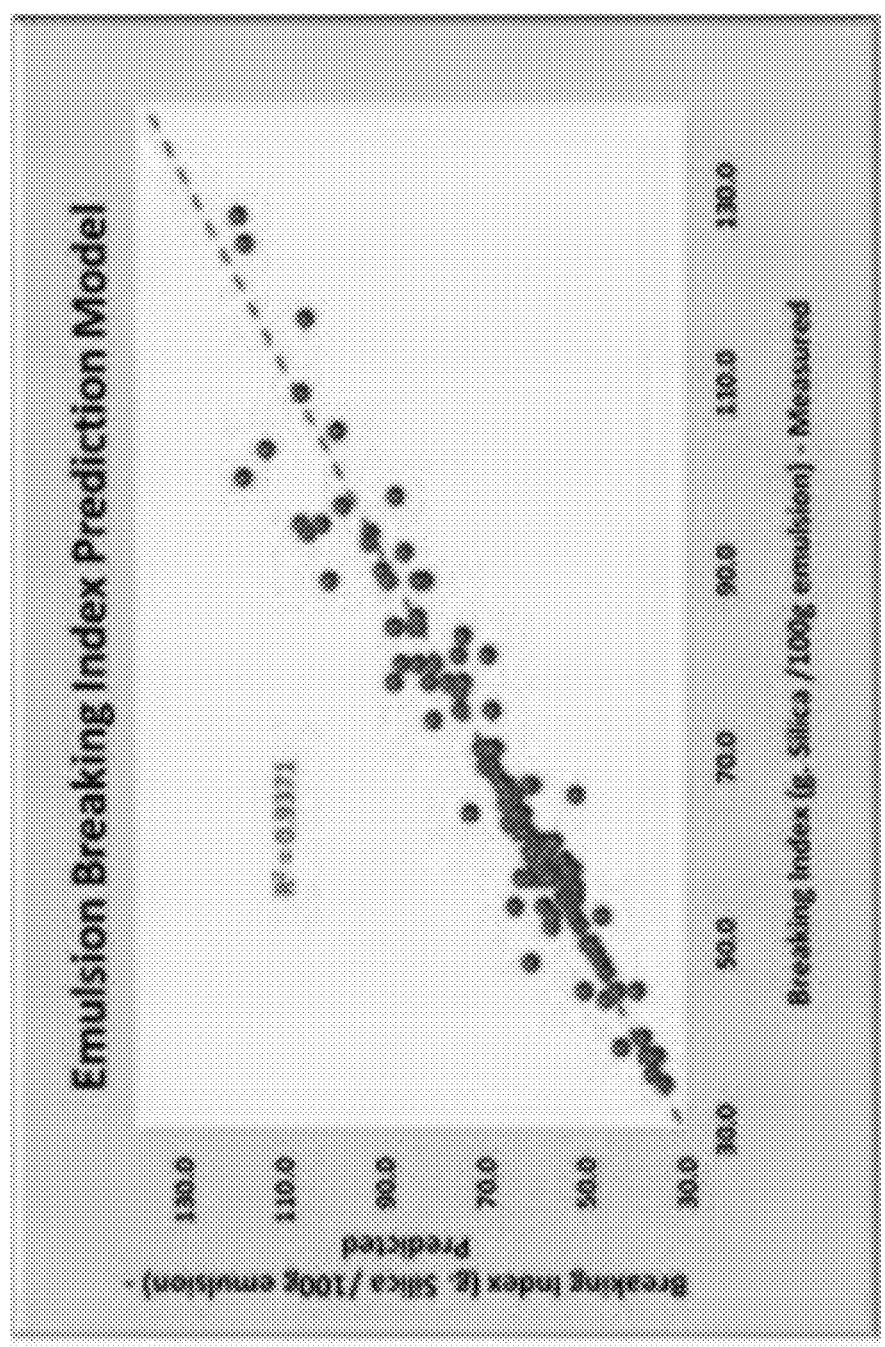
FIG. 4 shows a comparison of measured and calculated breaking index values for a variety of asphalt emulsions.

FIGS. 3 and 4 demonstrate the benefit of the unexpected discovery that emulsion properties for an asphalt fraction can be predicted based on linear combinations of predictions for the individual asphalt components. In FIG. 3, predictions of kinematic viscosity for a large number of asphalt emulsions are displayed relative to the corresponding measured kinematic viscosity values for the asphalt emulsions. It is noted that the "measured" kinematic viscosity values were derived from measured pseudo-viscosity values. FIG. 4 provides a similar type of comparison for prediction of breaking index versus measured breaking index for various emulsions. As shown in FIGS. 3 and 4, the predicted emulsion properties had a strong correlation with the corresponding measured values. The data in FIGS. 3 and 4 demonstrate the success in predicting properties of asphalt emulsions based on a linear combination of predicted values for the individual asphalt components in the asphalt fraction used to form the emulsion.

Asphalt Feedstocks

Some feedstocks in accordance with the present invention are heavy oils that include at least a portion of asphaltenes. Such heavy oils are suitable, possibly after additional distillation, for making an asphalt. Asphalt is a viscoelastic semi-solid bituminous material derived from the distillation residue of crude petroleum. Asphalt may be obtained from a variety of crude oil sources or fractions, including straight run vacuum residue, mixtures of vacuum residue with diluents such as vacuum tower wash oil, paraffin distillate, aromatic and naphthenic oils and mixtures thereof, oxidized vacuum residues or oxidized mixtures of vacuum residues and diluent oils and the like. Because it is hydrophobic and has good adhesive and weathering characteristics, asphalt is widely used as a binder or cement for stone or rock aggregate in pavement construction (typically only about 5 wt % of the mixture). Other feedstocks suitable for use in the invention include whole or reduced petroleum crude oils, atmospheric residua feedstocks, and vacuum residua feedstocks.

One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point or distillation point for a feed is defined as the temperature at which 5 wt % of the feed will boil or distill off during distillation. Similarly, a "T95" boiling point or distillation point is defined as the temperature at which 95 wt % of the feed will boil.

A typical feedstock for forming asphalt can have a normal atmospheric boiling point of at least 350° C., more typically at least 400° C., and will have a penetration range from 20 to 500 dmm at 25° C. (ASTM D-5). Alternatively, a feed may be characterized using a T5 boiling point, such as a feed with a T5 boiling point of at least 350° C., or at least 400° C., or at least 440° C.

Another example of a feedstock suitable for forming asphalt is a feedstock derived from an atmospheric resid fraction or a similar petroleum fraction. For example, when a whole crude oil, partial crude oil, or other feedstock is processed in a refinery, one common type of processing is to distill or fractionate the crude oil based on boiling point. One type of fractionation is atmospheric distillation, which can result in one or more fractions that boil at less than 650° F. (343° C.) or less than 700° F. (371° C.), and a bottoms fraction. This bottoms fraction corresponds to an atmospheric resid.

The bottoms fraction from atmospheric distillation can then be separated or fractionated using vacuum distillation. This generates one or more (vacuum) gas oil fractions and a vacuum resid fraction. Because the vacuum distillation is typically performed on a resid from atmospheric distillation, a vacuum gas oil fraction can be defined as a fraction with a T10 boiling point of at least 650° F. (343° C.), such as at least 700° F. (371° C.). Preferably, a vacuum gas oil fraction can have a T5 boiling point of at least 650° F. (343° C.), such as at least 700° F. (371° C.). The vacuum resid fraction may be suitable for use as an asphalt. The distillation cut point for forming the vacuum bottoms fraction can be selected based on a desired amount of vacuum gas oil and/or a desired quality for the asphalt fraction. Selecting a higher temperature cut point can increase the amount of a vacuum gas oil. However, such a higher temperature cut point will typically reduce the quality of the corresponding asphalt. Since both vacuum gas oil yield and asphalt quality are also dependent on the nature of the feedstock, the temperature cut point to achieve a desired combination of vacuum gas oil yield and asphalt quality will vary. A suitable cut point for the vacuum bottoms fraction to achieve a desired asphalt quality and/or to achieve a desired vacuum gas oil yield can be at least 750° F. (399° C.), such as at least 950° F. (510° C.) or at least 1050° F. (566° C.).

Modeling Properties of an Asphalt Fraction

Performing a distillation on a feed containing multiple feed components will typically result in an asphalt fraction where the ratios of the various crude sources in the asphalt fraction will differ from the ratios of the various crude sources in the feed. This is due to the different boiling point profiles for each crude source in the slate used to form a feed. For example, consider a feed containing equal weights of feed components (i.e., a 1 to 1 ratio) from two crude sources. In this example, the first crude source has a lower temperature boiling point profile. When a distillation is performed on such a feed to generate, for example, a vacuum gas oil fraction and an asphalt fraction, the ratio of the first asphalt component to the second asphalt component in the asphalt fraction will typically be less than 1 to 1.

The boiling point profile for each crude oil in a crude slate can be used to determine the ratio of asphalt components present in an asphalt fraction that is generated from the crude slate. One option for determining the relative proportion of each asphalt component in an asphalt fraction can be to determine, based on boiling point profile, the amount of each crude component that boils above the selected cut point for forming the asphalt fraction. More generally, any convenient method can be used for determining the proportion of each asphalt component within the asphalt fraction. This can include, for example, measuring a property such as kinematic viscosity of the resulting asphalt fraction, and then using that measured property to identify a "virtual" cut point corresponding to the asphalt composition, as described in U.S. Pat. No. 9,208,266. (U.S. Pat. No. 9,208,266 is incorporated herein by reference for the limited purpose of describing how to determine a virtual cut point, and how to determine a corresponding weighting of asphalt components within an asphalt fraction based on such a virtual cut point.)

In addition to determining the relative amounts of asphalt components in an asphalt fraction, a characterization of each asphalt component is also needed for incorporation into the model. Based on the goal of the model to provide properties for asphalt emulsions, the characterization of the asphalt components can be based on direct characterization of the asphalt components, characterization of the asphalt components as part of an emulsion, or a combination thereof. Preferably, the characterization can correspond to characterization of the asphalt component in an emulsion. This can include, for example, determination of the viscosity and/or the breaking point for a plurality of emulsions where the asphalt fraction in the emulsion includes at least a portion of the asphalt component. Asphalt components can then be deconvoluted from the asphalt fraction. Additionally or alternately, this can include determination of properties (such as viscosity and breaking point) for emulsions where the asphalt fraction corresponds to a single asphalt component. More generally, the emulsion properties determined during characterization for fitting the model can optionally but preferably correspond to the emulsion properties that are desired for prediction with the model.

The measured values can then be used to develop a model that correlates an initial set of inputs with the desired emulsion property outputs. In some aspects, the desired outputs can correspond to an emulsion viscosity and a breaking index. The emulsion viscosity can correspond to a kinematic viscosity, as calculated from an STV pseudo-viscosity determined according to EN 12846-1. The breaking index can correspond to an emulsion breaking index determined according to NF EN 13075-1.

For the input parameters, one aspect corresponds to the asphalt components in an asphalt fraction. It has been discovered that the emulsion properties of an asphalt fraction can be represented by a weighted linear combination of the emulsion properties of the asphalt components, where the emulsion properties of the asphalt components are represented as a polynomial, such as a polynomial having an "A+Bx" format. A and B can correspond to constants associated with a given property of an asphalt component. The variable "x" can be based on the virtual cut point for the asphalt fraction, and thereby can represent the conditions used for formation of each asphalt component within the asphalt fraction. In some aspects, the conditions used for formation of the asphalt fraction can be correlated with the penetration value of the asphalt.

Other input parameters can correspond to asphalt emulsion production parameters. As noted above, these include, but are not limited to, a water content for the emulsion, temperatures for one or more components of the emulsion, and/or the amount and type of emulsifier. The values for the asphalt emulsion production parameters can correspond to traditional values for production of asphalt emulsions. For example, the water content can be 15 wt % to 50 wt %; the emulsifier content can be 0.01 wt % to 1.5 wt %; the asphalt fraction temperature (when blended with the water phase for producing emulsion) can be 70° C. to 200° C.; the emulsifier or soap temperature (when added to the emulsion) can be 10° C. to 100° C.; and the emulsification temperature can be 70° C. to 140° C. For the type of emulsifier, one option can be to characterize individual emulsifiers, such as individual commercially available emulsifiers. Another option can be to only represent the emulsifier category, such as emulsifiers corresponding to alkyl diamines. A preferred last option can be the use of least squares regression or other multivariable regression methods for fitting a data set to a large plurality of variables. Such approach applied to a plurality of emulsions produced from a single emulsifier category under multiple formulation conditions (asphalt fraction, concentration, water content . . . ), can result in the determination of emulsifier indices ($I_{Ei}^{P1}$, $I_{Ei}^{P2}$, . . . ) specific to an emulsifier category in terms of impact on targeted emulsion property to be predicted.

Once the functional form for the correlation between the asphalt fraction, the emulsion input values, and the output prediction values has been selected, any convenient method can be used determine the model values for each asphalt component (such as the "A" and "B" values for asphalt components represented by an "A+Bx" form). Suitable methods can include, but are not limited to, least squares regression or other multivariable regression methods for fitting a data set to a large plurality of variables.

Asphalt Emulsion Formulation Tool

After developing a correlation model between the asphalt fraction (as a linear combination of the asphalt components within the asphalt fraction), the emulsion input parameters, and the desired output asphalt emulsion properties, the model can be used for prediction of asphalt emulsion properties based on selection of an asphalt fraction and a set of emulsion input parameters. One example of using the model can be incorporation of the model as part of a tool determining formulating an emulsion based on an asphalt fraction from a new crude slate and/or formed using a different cut point during distillation.

In an asphalt emulsion formulation tool, two types of input can be provided by a user of the tool. The first type of input corresponds to the nature of the asphalt fraction, which includes the asphalt components plus the cut point for forming the asphalt fraction. Optionally, the cut point provided to the model can be a virtual cut point. Optionally, a virtual cut point can be calculated based on specifying a measured distillation cut point and a refinery source, a distillation configuration, or a combination thereof. This first type of input corresponds to input parameters that cannot be readily change during emulsion formulation. The second type of input corresponds to the emulsion input parameters, such as the temperatures associated with forming the emulsion, the amount of water, and the amount and type of surfactant. This second type of emulsion formulation parameter represents a parameter that could be readily modified when attempting to formulate an emulsion based on an asphalt fraction.

Based on the first type of input (asphalt fraction-related) and the second type of input (emulsion formulation-related), the model can first provide output values for an emulsion that would be made from the asphalt fraction based on the input parameters as provided. The tool can then be used to compare the properties for the emulsion using the as-provided input parameters with a target set of desired properties for the emulsion. For example, it may be desirable to have both an emulsion breaking point and an emulsion viscosity that are within a range of values.

An example of a desired range of values can correspond to a range of emulsion property values for previously formulated asphalt emulsions that have resulted in desirable commercial performance. Such a desired range of values can be, for example, dependent on the refinery used for producing an asphalt fraction. If the emulsion from the as-provided input parameters is outside of the target range of values for at least one predicted value, the tool can provide a suggestion for how to modify the emulsion formulation inputs to form an emulsion with properties inside the target range of values. The suggested input values can be generated by any convenient method, depending on the nature of the correlation between the input parameters and the predicted output values. For example, the suggested input values could be generated by performing a sensitivity analysis on one or more of the as-provided input values in order to determine what type of changes would move the emulsion properties toward the target range of values. As another example, a commercial solver can be used to perform a constrained optimization on the emulsion formulation input parameters.

As another example, it may be desirable to form an asphalt emulsion that has an increased likelihood of providing properties similar to an emulsion formed from other asphalt fractions that have been used. Conventionally, producing asphalt emulsions that are successful for one or more desired applications has involved a substantial amount of testing. Part of this testing was to verify that an asphalt emulsion would behave in a stable manner when minor or typical variations were present either in the asphalt fraction, in the conditions for formation of the asphalt emulsion, or in the conditions for use for the asphalt emulsion. Based on the testing used for determining that an asphalt fraction generated desirable asphalt emulsions, it can be expected that such an asphalt fraction would be suitable for generating desirable asphalt emulsions under other conditions. Based on this expectation, a goal of an asphalt emulsion prediction tool can be to identify emulsion formation conditions for a new asphalt fraction so that the resulting emulsion has behavior similar to the behavior for a previously desirable asphalt fraction under the same or similar conditions. Conventionally, such a comparison can be challenging, as the emulsion formation conditions for the new asphalt fraction may not be the same (or sufficiently similar) to the emulsion formation conditions for the prior asphalt emulsions to allow for direct comparison.

In order to facilitate comparison between an emulsion from a new asphalt fraction and emulsions based on prior asphalt fractions, the asphalt emulsion prediction tool can be used to determine the emulsion properties for both the new asphalt fraction and the prior asphalt fractions under the specified set of emulsion formation conditions. The emulsion properties for the new asphalt fraction can then be represented as a point in a phase space. The emulsion properties for each prior asphalt fraction can also correspond to a point in phase space. In order to assist a user in understanding the data, a bounding shape can be developed, so that all or substantially all (such as at least 90%) of the prior asphalt fractions are contained within the bounding shape in the phase space. The emulsion properties for the new asphalt fraction can then be compared with the bounding shape. If the point corresponding to the new asphalt fraction is outside of the bounding shape, it may be desirable to make small changes to the emulsion formulation conditions to bring the emulsion based on the new asphalt fraction inside the bounding shape. Alternatively, it may be desirable to select a different set of emulsion formation conditions, resulting in a different location and/or geometry for the bounding shape.

Figure 5:
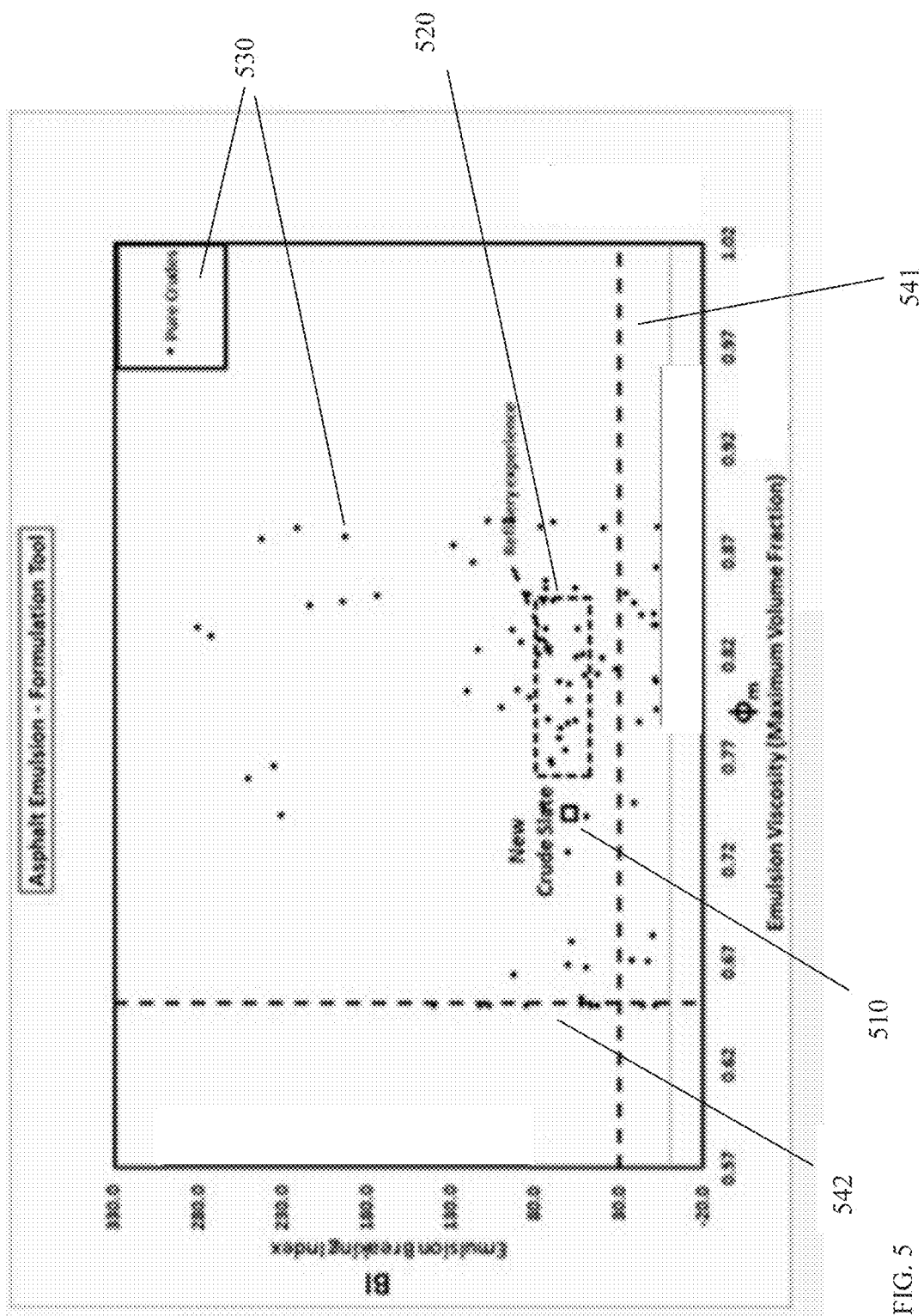
FIG. 5 shows an example of an interface for an asphalt emulsion property prediction tool.

FIG. 5 shows an example of an asphalt emulsion formulation tool that can be used to develop conditions for forming an asphalt emulsion based on an asphalt fraction that differs from any prior asphalt fractions used for making a desired emulsion. This can be referred to as a new crude slate. In the example shown in FIG. 5, the crude components in the new crude slate correspond to crude components that were previously in the model. One reason a crude slate can correspond to a new crude slate is if the crude slate corresponds to a virtual cut point temperature that has not been used before in making an emulsion for a previously known combination of crude components. For example, if the same combination of crude components is distilled at two different refineries, even if the same "actual" distillation (cut point) temperature is used at each refinery, differences in the equipment configuration between the refineries can result in a difference in the virtual cut point temperature for the asphalt fraction. Another reason a crude slate can correspond to a new crude slate is when the crude slate corresponds to a mixture of crude components that has not been used in combination before and/or a different ratio of crude components. Still another reason a crude slate can correspond to a new crude slate is when one or more of the crude components in a new crude slate corresponds to new crude components. In order to use the model when a new crude component is present, the new crude component can be characterized by forming several asphalt emulsions including the new crude component and developing model parameters for the asphalt component derived from the crude component.

To use the asphalt emulsion formulation tool, a value related to the virtual cut point of the asphalt fraction, such as the penetration value of the asphalt fraction, can be specified. Based on that virtual cut point, the formulation tool can calculate properties for an emulsion formed from each asphalt component in the asphalt fraction at a given set of conditions for forming an emulsion. The corresponding properties for an emulsion formed from the asphalt fraction can then be calculated based on a linear combination (based on weight percent in the fraction) of the calculated properties for the asphalt components.

FIG. 5 shows an example of this type of prediction. In FIG. 5, it is desired to predict the emulsion breaking index and the emulsion viscosity (as correlated with maximum volume fraction) for a new crude slate. In FIG. 5, various data points 530 (breaking index versus maximum volume fraction) are shown corresponding to emulsions made from individual asphalt components having the specified penetration value. The data point for new crude slate 510 corresponds to the predicted combination of emulsion property values based on a linear combination of the breaking index values and the maximum volume fraction values for the individual components in the asphalt fraction corresponding to new crude slate 510. The bounding box 520 in FIG. 5 corresponds to a bounding shape for emulsions based on asphalt fractions produced by a the refinery used for making the new crude slate that have previously been used to make "successful" asphalt emulsions. In this example, "successful" asphalt emulsions simply represent emulsions that were eventually deemed suitable by a customer for the desired end use. Of course, any other convenient definition could be used to define bounding box 520. It is noted that the "successful" emulsions formed from asphalt fractions at each refinery may differ, so the shape of bounding box 520 can potentially vary depending on the particular refinery used for forming an asphalt fraction at the same emulsion formation conditions. As shown in FIG. 5, the emulsion formation conditions specified, such as the wt % water, asphalt temperature during mixing, and water/soap temperature during mixing, result in an asphalt emulsion with a predicted combination of breaking index and viscosity (maximum volume fraction) that is outside of the prior "successful" experience from the specified refinery. In addition to showing the data point for new crude slate 510, the data points 530 for the various asphalt components available in the model, and the bounding box 520 for "successful" emulsions, FIG. 5 also provides two guidance or boundary lines 541 and 542. Guidance or boundary line 541 corresponds to a minimum breaking index value. Emulsions with breaking index values below boundary line 541 are likely to be unstable. Similarly, guidance or boundary line 542 corresponds to a maximum viscosity, as emulsions with viscosities greater than guidance or boundary line 542 are likely to be too viscous to form a stable emulsion.

Figure 6:
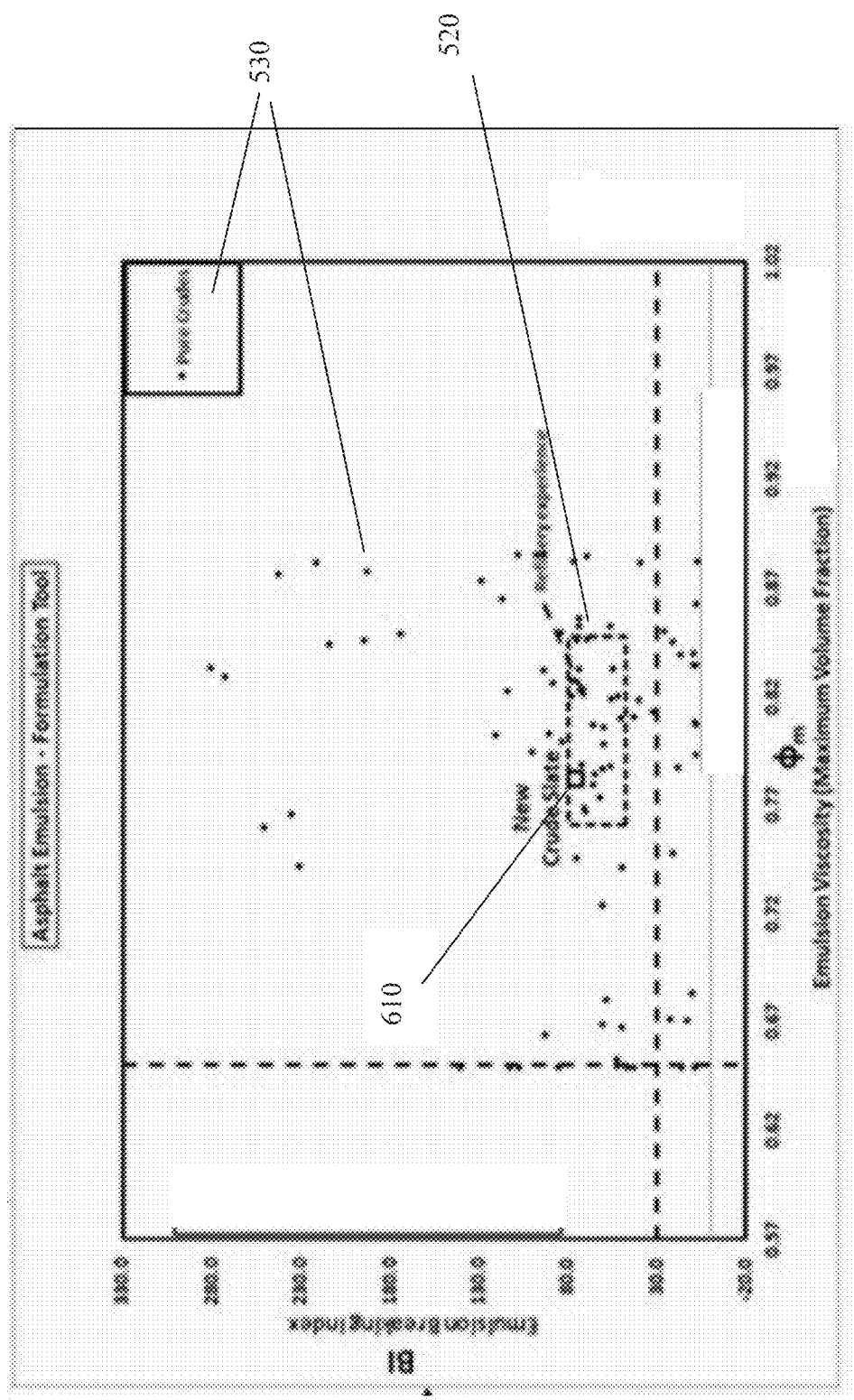
FIG. 6 shows an example of an interface for an asphalt emulsion property prediction tool after generation of a modified set of emulsion formation conditions.

In the example shown in FIG. 5 the predicted emulsion properties for the asphalt fraction from new crude slate 510 are outside of the desired bounding box 520. In order to find a set of emulsion conditions that can allow for production of a more desirable emulsion, an optimization tool (such as a linear solver) can be used to perform a constrained optimization on the conditions for forming the emulsion (temperatures, water content, amount of emulsifier) to identify conditions for forming an emulsion within the bounding box. FIG. 6 shows an example of the changes in conditions identified during the constrained optimization. As in FIG. 5, the emulsion properties for the new crude slate were determined by first calculating the emulsion properties for the individual components in the new crude slate. A linear combination of the components was then used to calculate the emulsion properties for the new crude slate. In the example shown in FIG. 6, it was feasible to make an emulsion using the new crude slate 610 that had a combination of breaking index and viscosity (maximum volume fraction) that was within the desired bounding box 520. Table 1 shows the changes in emulsion formation conditions determined using the constrained optimization.

TABLE 1

Constrained Optimization of Emulsion Formation Conditions

| | Original Formulation | Proposed Optimized Formulation |
|---|---|---|
| Vol % Water | 35.0 | 36.0 |
| Emulsifier amount (kg/ton emulsion) | 1.5 | 1.7 |
| Asphalt Temperature (° C.) | 150.0 | 130.0 |
| Soap/Water Temperature (° C.) | 50.0 | 53.2 |
| Emulsion Temperature (° C.) | 98.1 | 89.4 |

Based on the constrained optimization, all five of the parameters that were allowed to vary were modified in order to arrive at an emulsion within desired bounding box 520. In various aspects, the constrained optimization can be performed on any convenient subset of the input parameters. It is noted that in the example shown in FIGS. 5 and 6, the parameters related to the crude slate/asphalt fraction were not included as part of the optimization, since the asphalt fraction can often represent an input component that is formed at a separate location than the location for making an asphalt emulsion. However, if desired, the virtual cut point (or another related parameter such as penetration value)

could be allowed to vary as part of the constrained optimization. It is also noted that for the constrained optimization shown in FIG. 6, the bounding box 520 was not recalculated using the new emulsion parameters. In an alternative aspect, the bounding shape can be recalculated when performing a constrained optimization on emulsion formation conditions.

Figure 7:
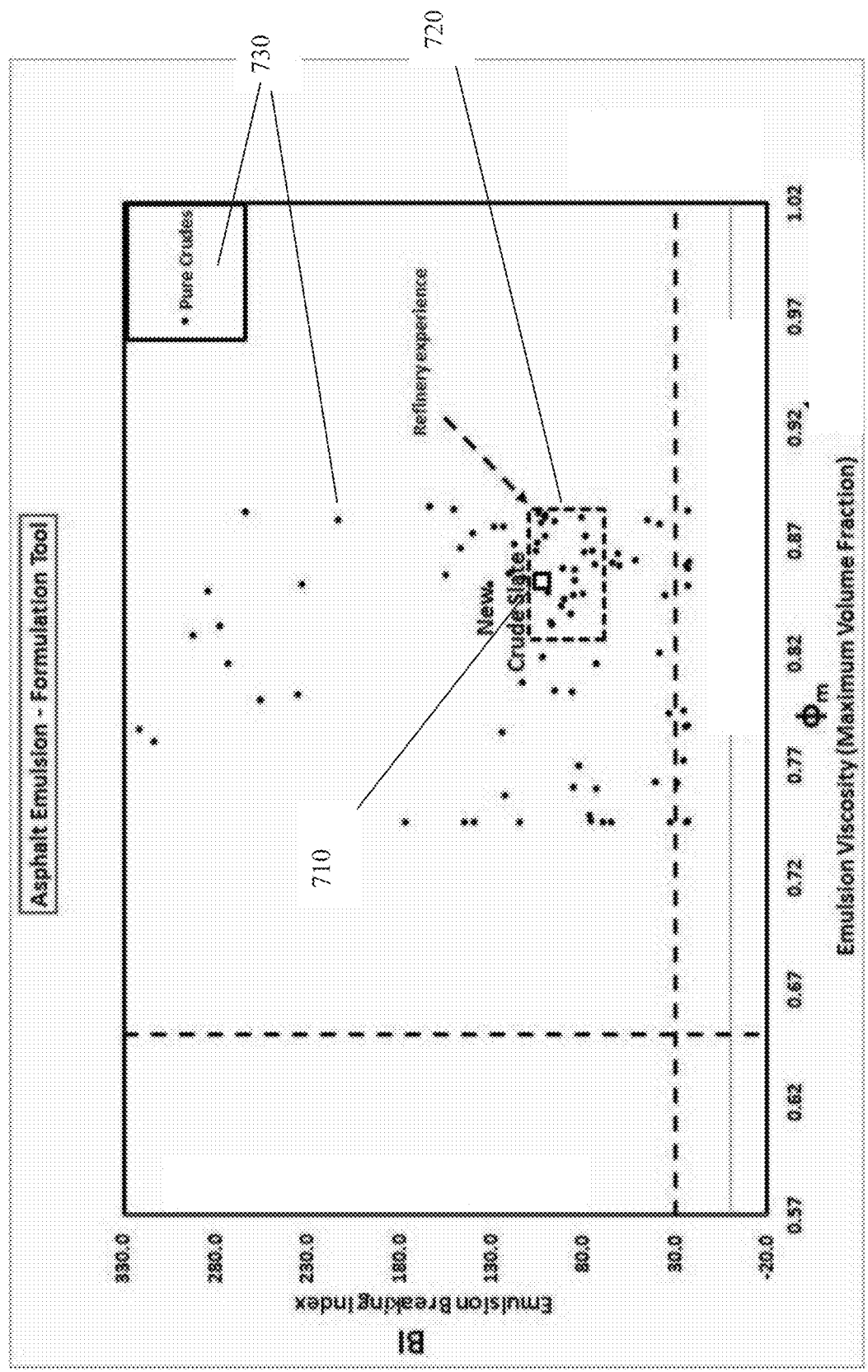
FIG. 7 shows an example of an interface for an asphalt emulsion property prediction tool after generation of a further modified set of emulsion formation conditions.

For the example shown in FIGS. 5 and 6, one way to test the new proposed formulation conditions can be to see if the new proposed formulation conditions remain within the bounding box 520 when the emulsifier is changed. In this type of test, all of the other emulsion formation conditions (temperatures, concentrations) remain the same, with only the emulsifier being changed. FIG. 7 shows how a change in the emulsifier impacted the shape and location of the bounding box 720 while also showing the emulsion formed from the new crude slate 710 remained within bounding box 720 after the change in emulsifier. It is noted that the data points 730 corresponding to the asphalt components represented in the model also have different positions based on the change in emulsifier.

Predictive Model Refinements

As noted above, the portion of the model related to representing an asphalt component can include a plurality of parameters that are fit to historical data for formulation of emulsions. These parameters are fit based on historical data for asphalt fractions from individual crude sources as well as asphalt fractions containing a plurality of asphalt components. However, individual crude sources can change over time, such as due to changes in the composition of the actual crude source or changes in how the crude source is extracted and/or pre-processed at the source. To reflect such changes, the fit parameters in the model can continue to be updated as more data becomes available. Additionally, as time passes, data that is sufficiently old can either be given a reduced weight during a fitting procedure or even omitted entirely.

Another potential modification can be to add additional new asphalt components to the historical data used for the fitting procedure. The new asphalt component(s) can be added as part of an emulsion made from a single component, or the new asphalt component(s) can be incorporated as part of an asphalt fraction containing multiple components.

Still another potential modification is to expand a model to incorporate data from more refineries that have formed asphalt fractions from a given crude source. In some embodiments, the data in the model can be based on forming asphalt fractions at a single refinery from various crude sources. However, data from multiple refineries can be incorporated into a single model if desired. The data from each refinery can be given the same weight, or the data can be weighted based on the refinery the model is being used at, so that historical data from the refinery currently making a prediction is given greater weight than data from other refineries. Incorporating data from multiple refineries can allow information about a given crude source and/or interactions of pairs of crudes to be built up in a more rapid manner.

FIG. 1 shows an example of constructing a predictive model that includes at least some of the model refinements described above. In FIG. 1, a crude slate 2 specifies a type and amount for a plurality of feed components 1 that are included in a feed for forming an asphalt fraction. In FIG. 1, each feed component 1 is represented by a designation (alpha, beta, etc.) The crude slate 2 represents the proportion of various feed components 1 within a particular feed. Based on a cut point 3, an asphalt component yield 4 can be determined at the cut point 3 for each of the feed components 1 within a resulting asphalt fraction 5. Due to differences in the boiling ranges of various feeds, the weight ratios of the components 1 within a crude slate 2 are likely to differ from the yields of the corresponding asphalt components 4 in an asphalt fraction 5. The yields of the asphalt components 4 in an asphalt fraction 5 can then be normalized, for example, to determine the composition of asphalt fraction 5.

It is noted that the cut point used for determining the asphalt component yields 4 in an asphalt fraction 5 can be dependent on factors other than a cut point temperature. For example, it is generally understood that vacuum distillations of a feed to form an asphalt fraction are non-ideal. As a result, the relationship between a cut point for forming an asphalt fraction and the resulting distillation profile for the asphalt fraction can depend on the nature of the vacuum distillation equipment. Thus, if the same crude slate is used to form an asphalt at two different refineries, the distillation profiles of the resulting apshalts will likely differ based on any differences that exist between the vacuum distillation configurations in the two refineries. To account for this, a virtual cut point can be used when determining the asphalt composition from a feed, where the virtual cut point differs from the temperature set as the cut point at a refinery. The virtual cut point can be determined, for example, based on the viscosities of asphalt fractions derived from various crude slates at a single refinery, or based on functional relationships 7 between the asphalt fraction and the asphalt components for other physical and/or chemical properties. The viscosities of the asphalt fractions from the various crude slates can be compared with viscosity calculations to identify any variations between the measured viscosity and the expected viscosity based on the individual components in an asphalt. Any variations can be used to determine an adjustment to the distillation cut point used by a refinery. This adjustment can then be used to determine a virtual cut point for determination of the composition of asphalt fractions formed from new crude slates and/or formed at new refinery cut point temperatures.

Based on the composition of asphalt fraction 5, various properties and/or parameters 9 for the asphalt fraction 5 can be determined based on predetermined functional relationships 8 between the emulsion properties of individual asphalt components (as represented by parameters 6) in an asphalt fraction and the properties of the emulsion. Typically such functional relationships 8 can be based in part on the relative weight percentages of each asphalt component in an asphalt fraction.

During initial construction of a model, as well as at any other convenient time during use of a model, the calculated parameters 9 for an asphalt fraction and/or an emulsion made from an asphalt fraction can be compared with measured values for asphalt emulsions produced 10 from the asphalt fraction. If the measured values from testing 11 do not sufficiently match the predicted parameter values 9, then additional fitting of the model can be performed to update the parameters 6 used to represent each individual crude component and/or asphalt component. When sufficient agreement is achieved between the model and available data points used for fitting the model, the model can be used as part of an asphalt emulsion tool 12 as described herein.

Figure 2:
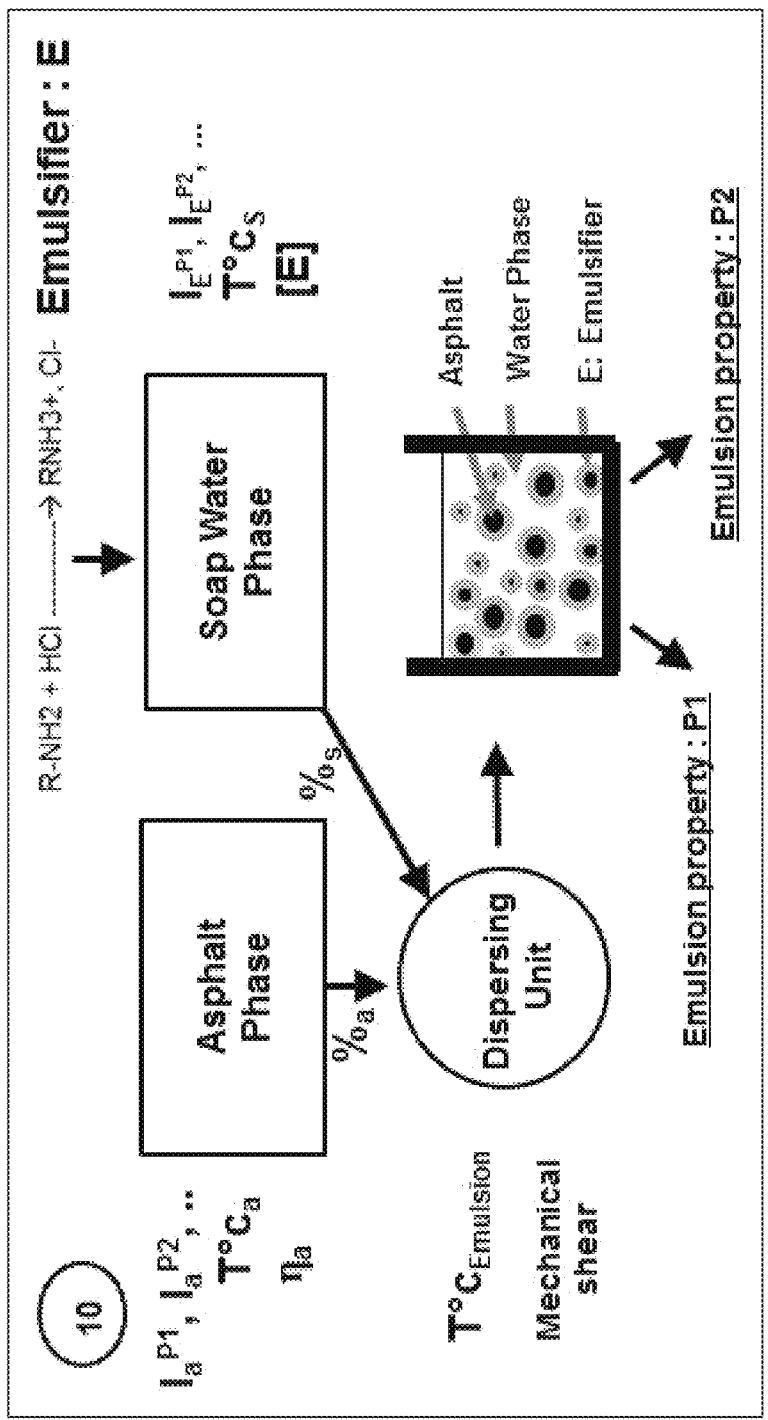
FIG. 2 shows a flowchart of creating a predictive model for key properties of asphalt emulsions produced from various asphalt and emulsifier natures according to an embodiment of the invention.

FIG. 2 provides an example of how the parameters from a model can be correlated with results 10 from asphalt emulsion production and testing. FIG. 2 schematically shows a process for forming an asphalt emulsion. As illustrated in FIG. 2, the inputs for forming an asphalt emulsion are an asphalt phase and a water phase. In the example shown in FIG. 2, the emulsifier for forming the emulsion is included with the water phase. The asphalt phase and water phase (including soap or other emulsifier) can be combined in a dispersing unit. The dispersing unit can correspond to, for example, a vessel that includes a mixer or other apparatus for providing shear forces to disperse the asphalt phase in the soap/water phase. The conditions for mixing in the dispersing unit, the amount and type of emulsifier, the temperature of the asphalt phase, and the temperature of the soap/water mixture can be selected to allow for control of the average size of the asphalt drops in the emulsion and/or control of the distribution of sizes of the asphalt drops in the emulsion. The resulting emulsion, corresponding to a dispersion of asphalt drops in water that are stabilized with emulsifier, can then be characterized to determine one or more properties of the emulsion.

During model fitting, the measured emulsion properties can be used to fit the model based on various parameters. FIG. 2 shows examples of the various types of input values and output properties that can be modeled and/or measured. For example, the input asphalt phase can be characterized based on the nature of the asphalt components in the asphalt fraction (including the cut point used for forming the asphalt components); the weight percentage of each asphalt component within the asphalt fraction; the viscosity of the asphalt fraction; and the temperature of the asphalt when the asphalt is mixed with the water phase to form the emulsion. The water phase can be characterized based on the type of each emulsifier (or optionally based on the specific emulsifier composition); the amount of each emulsifier; the temperature of the water phase when mixed with the asphalt phase to form the emulsion; and the amount of water. The dispersion unit can be characterized based on the temperature in the dispersion unit; and the severity of the mechanical shear. It is noted that input properties can typically correspond to properties that can both be measured and modeled. However, some input properties may correspond to parameters that are only modeled. For example, the actual cut point for forming an asphalt fraction can be measured, but the virtual cut points used in the model may differ from the actual cut point, and such virtual cut points could possibly be viewed as a parameter that is only modeled.

With regard to outputs, any convenient properties of the emulsion can be measured to allow for fitting of the model. For predictions from the model, it may be convenient to have the values predicted by the model be related to but different from the measured values. For example, the pseudo-viscosity (or another type of measured viscosity) for an emulsion can correspond to a property that is convenient to measure. The emulsion viscosity can be related to the amount of water versus the amount of asphalt in the emulsion and the distribution of droplet sizes in the emulsion. Attempting to measure the distribution of droplet sizes within an emulsion can potentially require a more involved, time-consuming technique. However, from a model prediction perspective, predicting the droplet size distribution may correspond to a more convenient parameter for prediction. For example, the droplet size distribution may have a simplified relationship to the input values for the model. In this type of situation, it can be beneficial to have the model predict the droplet size distribution, and then calculate a viscosity based on the predicted droplet size distribution. This would result in the measured value (viscosity) being different from but related to the predicted property (droplet size distribution) of the model. In other aspects, the desired property for measurement, such as breaking index under NF EN 13075-1, may correspond to an output parameter that is convenient to directly model.

Tool Implementation

Various functions described herein as being performed by one or more entities may be carried out by hardware, firmware, and/or software. For instance, various functions may be carried out by a processor executing instructions stored in memory.

Figure 8:
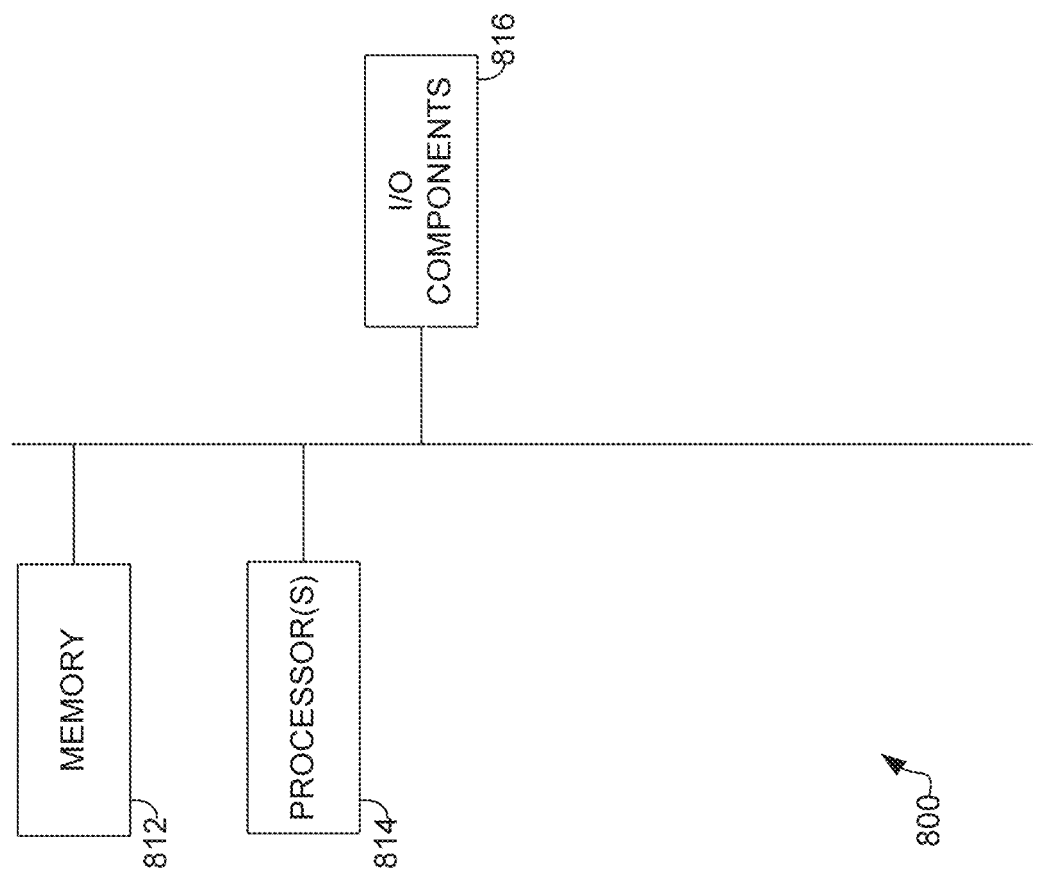
FIG. 8 schematically shows an example of a computing device.

An exemplary operating environment in which the model and/or asphalt emulsion formulation tool may be implemented is described below. Such an operating environment can generally be referred to as a computing device, such as the computing device 800 that is schematically illustrated in FIG. 8. The computing device 800 is intended to be illustrative only, and should not be interpreted as having any dependency or requirement relating to any one or combination of components illustrated.

The model and/or asphalt emulsion formulation tool may be described in the general context of computer code or machine-useable instructions, including computer-executable instructions such as program modules. Generally, program modules including routines, programs, objects, components, data structures, etc. refer to code that perform particular tasks or implement particular abstract data types. The invention may be practiced in any convenient computing environment, such as a stand-alone computing environment, a hand-held computing environment, and/or a distributed computing environment where tasks are performed by remote-processing devices that are linked through a communications network.

With reference to FIG. 8, computing device 800 can include one or more processors 814 and an associated memory 812. Optionally, the computing device 800 can further include typical features associated with a computing devices, which can generally be referred to as input/output components 816. Input/output components 816 can include components for presenting data/images, components for entering data (such as a touch screen and/or keyboard), and ports for connection with other computing devices.

Computing device 800 typically includes a variety of computer-readable media. Computer-readable media can be any available media that can be accessed by computing device 800 and includes both volatile and nonvolatile media, removable and non-removable media. In some aspects, the computer-readable media can include volatile and nonvolatile, removable and non-removable media implemented in any method or technology for storage of information such as computer-readable instructions, data structures, program modules or other data. For example, computer-readable media can include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 800. Additionally or alternately, computer-readable media can correspond to non-transitory computer-readable media and/or can correspond to media that excludes signals per se.

Memory 812 includes computer storage media in the form of volatile and/or nonvolatile memory. The memory may be removable, non-removable, or a combination thereof. Exemplary hardware devices include solid-state memory, hard drives, optical-disc drives, etc. Computing device 800 includes one or more processors that read data from various entities such as memory 812 or I/O components 816.

ADDITIONAL EXAMPLE

Figure 9:
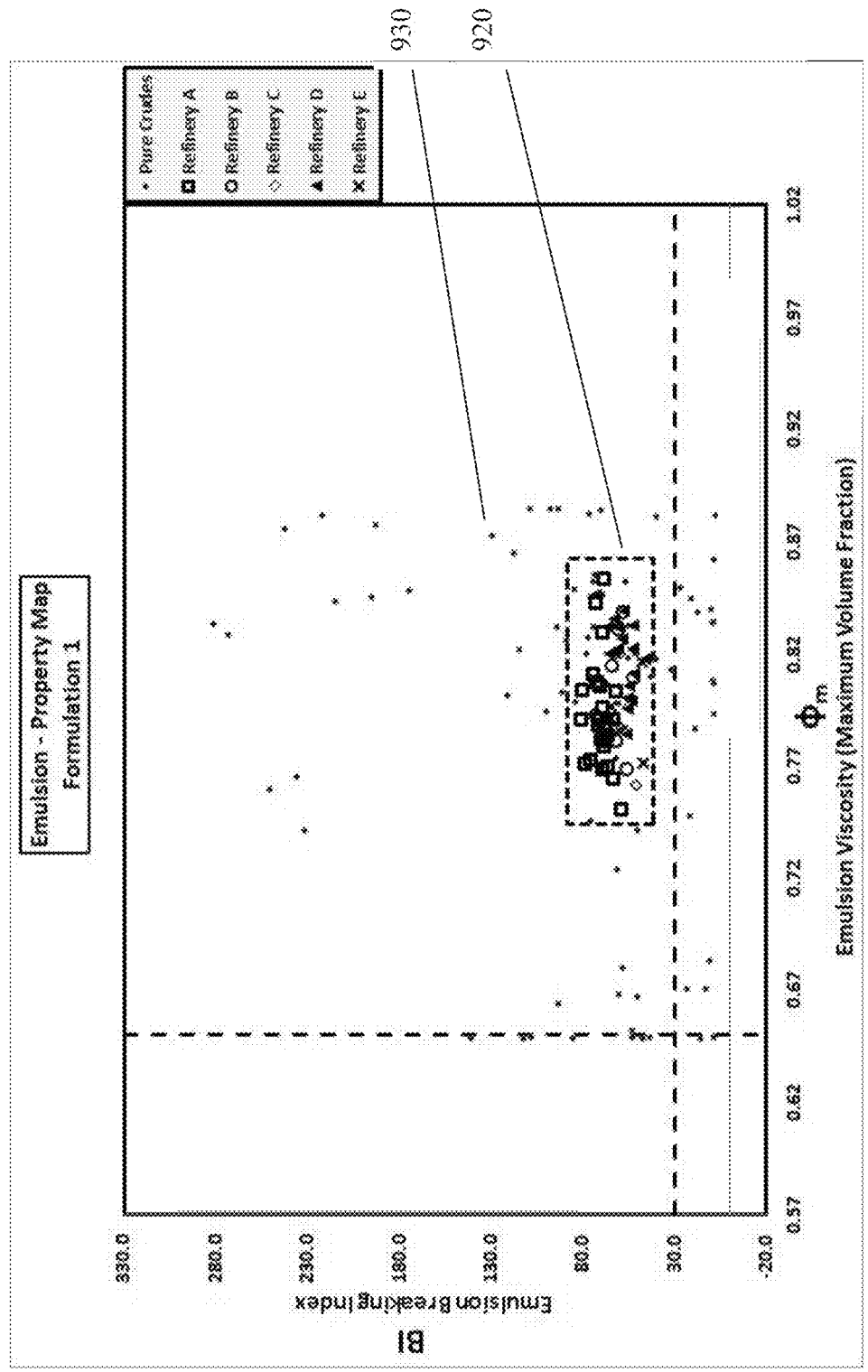
FIG. 9 shows an example of an interface for an asphalt emulsion property prediction tool.
Figure 10:
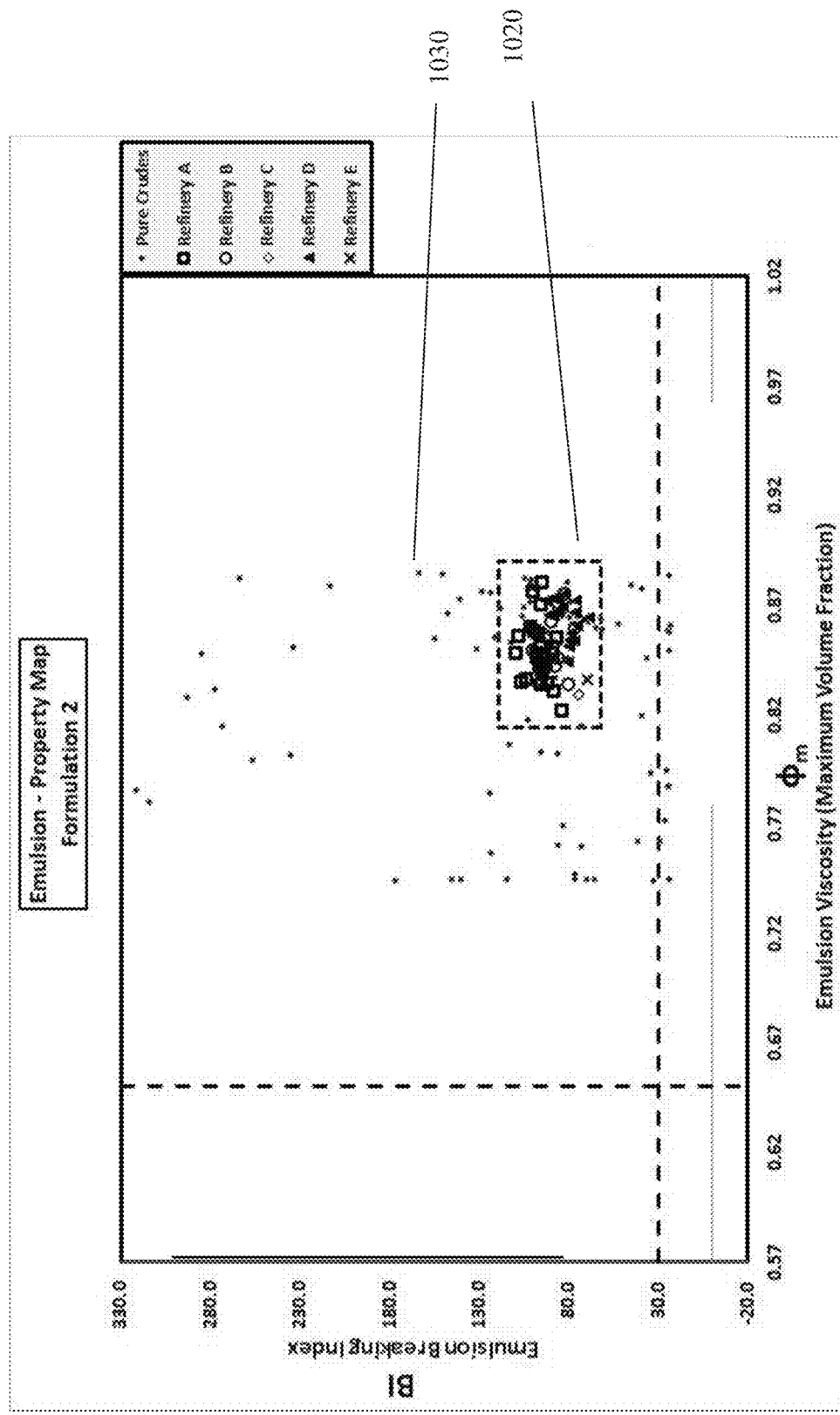
FIG. 10 shows an example of an interface for an asphalt emulsion property prediction tool after generation of a modified set of emulsion formation conditions.

FIGS. 9 and 10 illustrate another example of how the asphalt emulsion prediction tool can assist a user with visualization of the relationship between various asphalts. In FIG. 9, asphalt emulsion properties (breaking index; emulsion viscosity as correlated with maximum volume fraction) are shown for asphalt fractions produced from various refineries at a selected set of emulsion conditions. The emulsion conditions include use of a first emulsifier, which corresponds to an amido imidazoline type emulsifier. In FIG. 9, data points 930 are displayed for emulsions corresponding to the individual asphalt components represented in the model. A number of predicted values are also shown for emulsions based on asphalt fractions that have previously been generated by one of Refineries A-E. A bounding shape 920 is used to define a region that contains all of the emulsions based on the various refinery asphalt fractions. FIG. 10 provides a similar type of plot, but in FIG. 10 the emulsifier is changed to a tallow di-amine type emulsifier. All other emulsification conditions in FIG. 10 are the same as FIG. 9. In this example, the emulsification conditions included an emulsifier concentration of 1.5 g/L, an asphalt penetration grade of 195 dmm, and 35 vol % water.

Based on the change in the emulsifier, the data points 1030 corresponding to the asphalt components have a different distribution, and the grouping of the emulsions based on the refinery asphalt fractions results in a different shape for bounding box 1020. In particular, the relative shape of bounding box 920 versus bounding box 1020 shows that the amido imidazoline type emulsifier provides emulsions with higher viscosity but lower breaking index in comparison with the tallow di-amine emulsifier type. Additionally, the emulsion viscosity is less dependent on the nature of the asphalt for the amido imidazoline emulsifier type (i.e., the bounding box is narrower), while the breaking index is less dependent on the nature of the asphalt for the tallow di-amine emulsifier. Based on the bounding boxes 920 and 1020, the asphalt emulsion prediction tool can assist a user with visualizing how to, for example, reduce or minimize the variability in emulsions by selecting appropriate emulsion formation conditions. Additionally, by plotting only certain refineries as opposed to all available refineries, the asphalt emulsion prediction tool can allow for comparison between the asphalt fractions produced at different refineries to better understand the nature of the variance between refineries.

Additional Embodiments

Embodiment 1

A method for predicting asphalt emulsion properties, comprising: identifying a crude slate, the crude slate comprising crude components from a plurality of crude sources, the crude components being present in the crude slate in a first set of component weight ratios; calculating a second set of component weight ratios based on a cut point temperature for an asphalt fraction based on the crude slate, the asphalt fraction comprising asphalt components corresponding to the crude components, the asphalt components being present in the asphalt fraction in the second set of component weight ratios; receiving a first set of emulsion formulation input parameters corresponding to a first set of emulsion formulation conditions; calculating one or more first emulsion properties for each asphalt component in the asphalt fraction based on the first set of emulsion formulation input parameters and one or more fit parameters associated with each asphalt component; determining one or more first emulsion properties for the asphalt fraction, the one or more first emulsion properties for the asphalt fraction comprising a linear combination of the calculated one or more first emulsion properties for each asphalt component in the asphalt fraction, the linear combination being based on the second set of asphalt component weight ratios; modifying at least one of the emulsion formulation input parameters to form a modified set of emulsion formulation parameters; calculating one or more modified emulsion properties for each asphalt component in the asphalt fraction based on the modified set of emulsion formulation input parameters and the one or more fit parameters associated with each asphalt component; and determining one or more modified emulsion properties for the asphalt fraction, the one or more modified emulsion properties for the asphalt fraction comprising a linear combination of the calculated one or more modified emulsion properties for each asphalt component in the asphalt fraction, the linear combination being based on the second set of asphalt component weight ratios.

Embodiment 2

The method of Embodiment 1, wherein the cut point temperature comprises a cut point temperature for vacuum distillation of the feed; or wherein the cut point temperature comprises a virtual cut point temperature, the virtual cut point temperature being based on a vacuum distillation cut point temperature and at least one of a refinery identity and a vacuum distillation equipment configuration.

Embodiment 3

A method for predicting asphalt properties, comprising: forming a first asphalt emulsion from an asphalt fraction under a first set of emulsion formulation conditions, the asphalt fraction comprising asphalt components from a plurality of crude sources, the asphalt fraction being formed from separation of a feed comprising the plurality of crude sources at a cut point temperature to form a 538° C.+ fraction and processing the 538° C.+ fraction under asphalt formation conditions to form the asphalt fraction, the plurality of crude sources being present in the feed in a first set of component weight ratios; calculating a second set of component weight ratios for the asphalt components in the asphalt fraction, the second set of component weight ratios being based on the cut point temperature; receiving a first set of emulsion formulation input parameters corresponding to the first set of emulsion formulation conditions; calculating one or more first emulsion properties for each asphalt component in the asphalt fraction based on the first set of emulsion formulation input parameters and one or more fit parameters associated with each asphalt component; determining one or more first emulsion properties for the asphalt fraction, the one or more first emulsion properties for the asphalt fraction comprising a linear combination of the calculated one or more first emulsion properties for each asphalt component in the asphalt fraction, the linear combination being based on the second set of asphalt component weight ratios; modifying at least one of the emulsion formulation input parameters to form a modified set of emulsion formulation parameters; calculating one or more modified emulsion properties for each asphalt component in the asphalt fraction based on the modified set of emulsion formulation input parameters and the one or more fit parameters associated with each asphalt component; determining one or more modified emulsion properties for the asphalt fraction, the one or more modified emulsion properties for the asphalt fraction comprising a linear combination of the calculated one or more modified emulsion properties for each asphalt component in the asphalt fraction, the linear combination being based on the second set of asphalt component weight ratios; and forming a second asphalt emulsion from the asphalt fraction under a second set of emulsion formulation conditions corresponding to the modified set of emulsion formulation input parameters.

Embodiment 4

The method of any of the above embodiments, wherein the asphalt fraction comprises at least four asphalt components.

Embodiment 5

The method of any of the above embodiments, wherein the one or more fit parameters associated with each asphalt component in the asphalt fraction comprise coefficients for a polynomial having four or fewer terms.

Embodiment 6

The method of any of the above embodiments, wherein the one or more first emulsion properties comprise at least one of an emulsion viscosity, a maximum volume fraction, an emulsion breaking index, or a combination thereof, the emulsion viscosity optionally comprising a kinematic viscosity, a pseudo-viscosity, or a combination thereof.

Embodiment 7

The method of any of the above embodiments, wherein the emulsion input parameters comprise a water content, a type of emulsifier, an amount of emulsifier, one or more temperatures associated with forming an emulsion, or a combination thereof.

Embodiment 8

The method of any of the above embodiments, further comprising updating at least one fit parameter associated with an asphalt component based on a measured property of the first asphalt emulsion, the second asphalt emulsion, or a combination thereof.

Embodiment 9

The method of any of the above embodiments, further comprising displaying the one or more first emulsion properties for each asphalt component in the asphalt fraction; or further comprising displaying the one or more modified emulsion properties for each asphalt component in the asphalt fraction; or a combination thereof.

Embodiment 10

The method of any of the above embodiments, further comprising displaying one or more first emulsion properties for one or more asphalt components not present in the asphalt fraction; or further comprising displaying one or more first emulsion properties for one or more asphalt components not present in the asphalt fraction; or a combination thereof.

Embodiment 11

The method of any of the above embodiments, further comprising calculating one or more first emulsion properties for an additional plurality of asphalt fractions; and displaying a first bounding shape based on the calculated one or more first emulsion properties for the additional plurality of asphalt fractions.

Embodiment 12

The method of Embodiment 11, further comprising calculating one or more modified emulsion properties for the additional plurality of asphalt fractions; and displaying a modified bounding shape based on the calculated one or more modified emulsion properties for the additional plurality of asphalt fractions, the additional plurality of asphalt fractions optionally comprising asphalt fractions derived from a single refinery.

Embodiment 13

The method of Embodiment 11 or 12, wherein the determined one or more first properties for the asphalt fraction are outside the first bounding shape, wherein the determined one or more modified properties for the asphalt fraction are inside the first bounding shape, or a combination thereof.

Embodiment 14

The method of Embodiment 11 or 12, wherein modifying at least one of the emulsion formulation input parameters comprises performing a constrained optimization, the constrained optimization optionally being performed to determine modified emulsion formulation input parameters to produce an emulsion within at least one of the first bounding shape and the modified bounding shape.

Embodiment 15

An asphalt emulsion property prediction tool, comprising: a processor and an associated memory, the memory comprising computer-executable instructions that, when executed by the processor, provide a method comprising the method of any of Embodiments 1-13.

Additional Embodiment A. The tool of Embodiment 15, wherein receiving a set of component weight ratios comprises: receiving a cut point temperature and a first set of crude component weight ratios corresponding to weights of a plurality of crudes sources present in a feed; calculating a second set of asphalt component weight ratios for the asphalt components in the asphalt fraction, based on the cut point temperature, wherein the calculating one or more emulsion properties based on the set of component weight ratios comprises calculating one or more emulsion properties based on the second set of asphalt component weight ratios.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for predicting asphalt emulsion properties, comprising:
identifying a crude slate, the crude slate comprising crude components from a plurality of crude sources, the crude components being present in the crude slate in a first set of component weight ratios;
calculating a second set of component weight ratios based on a cut point temperature for an asphalt fraction based on the crude slate, the asphalt fraction comprising asphalt components corresponding to the crude components, the asphalt components being present in the asphalt fraction in the second set of component weight ratios;
receiving a first set of emulsion formulation input parameters corresponding to a first set of emulsion formulation conditions;
calculating one or more first emulsion properties for each asphalt component in the asphalt fraction based on the first set of emulsion formulation input parameters and one or more fit parameters associated with each asphalt component;
determining one or more first emulsion properties for the asphalt fraction, the one or more first emulsion properties for the asphalt fraction comprising a linear combination of the calculated one or more first emulsion properties for each asphalt component in the asphalt fraction, the linear combination being based on the second set of asphalt component weight ratios;
modifying at least one of the emulsion formulation input parameters to form a modified set of emulsion formulation parameters;
calculating one or more modified emulsion properties for each asphalt component in the asphalt fraction based on the modified set of emulsion formulation input parameters and the one or more fit parameters associated with each asphalt component;
determining one or more modified emulsion properties for the asphalt fraction, the one or more modified emulsion properties for the asphalt fraction comprising a linear combination of the calculated one or more modified emulsion properties for each asphalt component in the asphalt fraction, the linear combination being based on the second set of asphalt component weight ratios.

2. The method of claim 1, wherein the cut point temperature comprises a cut point temperature for vacuum distillation of the feed.

3. The method of claim 1, wherein the cut point temperature comprises a virtual cut point temperature, the virtual cut point temperature being based on a vacuum distillation cut point temperature and at least one of a refinery identity and a vacuum distillation equipment configuration.

4. The method of claim 1, wherein the asphalt fraction comprises at least four asphalt components.

5. The method of claim 1, wherein the one or more fit parameters associated with each asphalt component in the asphalt fraction comprise coefficients for a polynomial having four or fewer terms.

6. The method of claim 1, wherein the one or more first emulsion properties comprise at least one of an emulsion viscosity, a maximum volume fraction, an emulsion breaking index, or a combination thereof.

7. The method of claim 6, wherein the emulsion viscosity comprises a kinematic viscosity, a pseudo-viscosity, or a combination thereof.

8. The method of claim 1, wherein the emulsion input parameters comprise a water content, a type of emulsifier, an amount of emulsifier, one or more temperatures associated with forming an emulsion, or a combination thereof.

9. The method of claim 1, further comprising updating at least one fit parameter associated with an asphalt component based on a measured property of the first asphalt emulsion, the second asphalt emulsion, or a combination thereof.

10. The method of claim 1, further comprising displaying the one or more first emulsion properties for each asphalt component in the asphalt fraction; or further comprising displaying the one or more modified emulsion properties for each asphalt component in the asphalt fraction; or a combination thereof.

11. The method of claim 1, further comprising displaying one or more first emulsion properties for one or more asphalt components not present in the asphalt fraction; or further comprising displaying one or more first emulsion properties for one or more asphalt components not present in the asphalt fraction; or a combination thereof.

12. The method of claim 1, further comprising calculating one or more first emulsion properties for an additional plurality of asphalt fractions; and
displaying a first bounding shape based on the calculated one or more first emulsion properties for the additional plurality of asphalt fractions.

13. The method of claim 12, further comprising calculating one or more modified emulsion properties for the additional plurality of asphalt fractions; and
displaying a modified bounding shape based on the calculated one or more modified emulsion properties for the additional plurality of asphalt fractions.

14. The method of claim 13, wherein modifying at least one of the emulsion formulation input parameters comprises performing a constrained optimization.

15. The method or tool of claim 14, wherein the constrained optimization is performed to determine modified emulsion formulation input parameters to produce an emulsion within at least one of the first bounding shape and the modified bounding shape.

16. The method of claim 12, wherein the additional plurality of asphalt fractions comprise asphalt fractions derived from a single refinery.

17. The method of claim 12, wherein the determined one or more first properties for the asphalt fraction are outside the first bounding shape, wherein the determined one or more modified properties for the asphalt fraction are inside the first bounding shape, or a combination thereof.

18. An asphalt emulsion property prediction tool, comprising:
a processor and an associated memory, the memory comprising computer-executable instructions that, when executed by the processor, provide a method comprising:
identifying a crude slate, the crude slate comprising crude components from a plurality of crude sources, the crude components being present in the crude slate in a first set of component weight ratios;
calculating a second set of component weight ratios based on a cut point temperature for an asphalt fraction based on the crude slate, the asphalt fraction comprising asphalt components corresponding to the crude components, the asphalt components being present in the asphalt fraction in the second set of component weight ratios;

receiving a first set of emulsion formulation input parameters corresponding to a first set of emulsion formulation conditions;

calculating one or more first emulsion properties for each asphalt component in the asphalt fraction based on the first set of emulsion formulation input parameters and one or more fit parameters associated with each asphalt component;

determining one or more first emulsion properties for the asphalt fraction, the one or more first emulsion properties for the asphalt fraction comprising a linear combination of the calculated one or more first emulsion properties for each asphalt component in the asphalt fraction, the linear combination being based on the second set of asphalt component weight ratios;

modifying at least one of the emulsion formulation input parameters to form a modified set of emulsion formulation parameters;

calculating one or more modified emulsion properties for each asphalt component in the asphalt fraction based on the modified set of emulsion formulation input parameters and the one or more fit parameters associated with each asphalt component;

determining one or more modified emulsion properties for the asphalt fraction, the one or more modified emulsion properties for the asphalt fraction comprising a linear combination of the calculated one or more modified emulsion properties for each asphalt component in the asphalt fraction, the linear combination being based on the second set of asphalt component weight ratios.

19. The tool of claim 18, wherein receiving a set of component weight ratios comprises:

receiving a cut point temperature and a first set of crude component weight ratios corresponding to weights of a plurality of crudes sources present in a feed;

calculating a second set of asphalt component weight ratios for the asphalt components in the asphalt fraction, based on the cut point temperature, wherein the calculating one or more emulsion properties based on the set of component weight ratios comprises calculating one or more emulsion properties based on the second set of asphalt component weight ratios.

20. A method for predicting asphalt properties, comprising:

forming a first asphalt emulsion from an asphalt fraction under a first set of emulsion formulation conditions, the asphalt fraction comprising asphalt components from a plurality of crude sources, the asphalt fraction being formed from separation of a feed comprising the plurality of crude sources at a cut point temperature to form a 538° C.+ fraction and processing the 538° C.+ fraction under asphalt formation conditions to form the asphalt fraction, the plurality of crude sources being present in the feed in a first set of component weight ratios;

calculating a second set of component weight ratios for the asphalt components in the asphalt fraction, the second set of component weight ratios being based on the cut point temperature;

receiving a first set of emulsion formulation input parameters corresponding to the first set of emulsion formulation conditions;

calculating one or more first emulsion properties for each asphalt component in the asphalt fraction based on the first set of emulsion formulation input parameters and one or more fit parameters associated with each asphalt component;

determining one or more first emulsion properties for the asphalt fraction, the one or more first emulsion properties for the asphalt fraction comprising a linear combination of the calculated one or more first emulsion properties for each asphalt component in the asphalt fraction, the linear combination being based on the second set of asphalt component weight ratios;

modifying at least one of the emulsion formulation input parameters to form a modified set of emulsion formulation parameters;

calculating one or more modified emulsion properties for each asphalt component in the asphalt fraction based on the modified set of emulsion formulation input parameters and the one or more fit parameters associated with each asphalt component;

determining one or more modified emulsion properties for the asphalt fraction, the one or more modified emulsion properties for the asphalt fraction comprising a linear combination of the calculated one or more modified emulsion properties for each asphalt component in the asphalt fraction, the linear combination being based on the second set of asphalt component weight ratios; and forming a second asphalt emulsion from the asphalt fraction under a second set of emulsion formulation conditions corresponding to the modified set of emulsion formulation input parameters.

* * * * *